United States Patent [19]

Djuric et al.

[11] Patent Number: 4,730,078
[45] Date of Patent: Mar. 8, 1988

[54] ALLENIC PROSTACYCLINS

[75] Inventors: Stevan W. Djuric, Glenview; Masateru Miyano, Northbrook, both of Ill.

[73] Assignee: G. D. Searle & Co., Chicago, Ill.

[21] Appl. No.: 50,257

[22] Filed: May 13, 1987

[51] Int. Cl.[4] ............................................. C07C 177/00
[52] U.S. Cl. ...................................... 560/119; 560/56; 560/10; 562/466; 562/501
[58] Field of Search .................. 560/119, 56; 562/466, 562/501; 514/530, 573

[56] References Cited

U.S. PATENT DOCUMENTS

| | | | |
|---|---|---|---|
| 4,423,068 | 12/1983 | Li | 560/119 |
| 4,436,934 | 3/1984 | Larock | 560/119 |
| 4,487,960 | 12/1984 | Lin | 560/56 |
| 4,533,749 | 8/1985 | Aristoff et al. | 560/56 |
| 4,608,388 | 8/1986 | Kluge et al. | 560/119 |
| 4,618,626 | 10/1986 | Skuballa et al. | 560/119 |
| 4,678,805 | 7/1987 | Kluge | 560/119 |

Primary Examiner—Paul J. Killos
Attorney, Agent, or Firm—J. Timothy Keane; Paul D. Matukaitis

[57] ABSTRACT

The present invention relates to allenic prostacyclin derivatives of the formula:

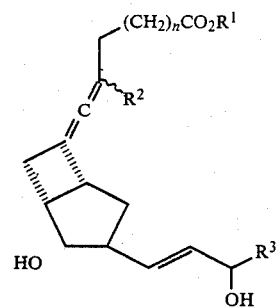

wherein:
n is 0, 1, 2
$R^1$ is hydrogen, lower alkyl, lower hydroxyalkyl, or a pharmaceutically acceptable cation;
$R^2$ is hydrogen, lower alkyl, cycloalkyl, heteroalkyl, halogen, aryl, alkylthio, phenylthio, alkylsulfinyl, phenylsulfonyl, or trifluoromethyl,
$R^3$ is a lower alkyl, a cycloalkyl, phenyl, benzyl, a cycloheteroalkyl, a lower alkyl having one to eight carbons substituted with one or more fluorines or containing 1 or 2 unsaturated bonds; and carbon 15 may be in the R or the S configuration, or a mixture of R and S with the proviso that when $R^1$ is a lower alkyl or lower hydroxyalkyl that carbon 15 is not in the R configuration.

These compounds are useful for the treatment of platelet dysfunction and atherosclerosis. Also disclosed is the process for preparing these compounds and their appropriate intermediates.

6 Claims, No Drawings

ALLENIC PROSTACYCLINS

BACKGROUND OF THE INVENTION

1. Field of the Invention

This invention relates to prostacyclin derivatives and to a process for preparing them. In particular, this invention relates to novel prostacyclin (PGI$_2$) derivatives. More particularly, this invention relates to PGI$_2$ derivatives such as allenic carbacyclins.

2. Description of Prior Art

Prostaglandins, prostacyclins, carbacyclins, and their analogs are well-known organic compounds derived from prostanoic acid.

As drawn hereinafter the formulas in accordance with the present invention represent a particular optically active isomer having the same absolute configuration as PGI$_2$. Except when R$^1$ is an carboxylic acid ester, both the R and S configuration at carbon 15 (bearing the hydroxyl group) or mixtures are included within the scope of this invention.

In the formulas, broken line attachments to the cyclopentane ring or side chain indicate substituents in alpha configuration, i.e. below the plane of the cyclopentyl ring or side chain. Heavy solid line attachments indicate substituents in beta configuration, i.e. above the plane.

For background on prostaglandins, see for example Bergstrom et al., *Pharmacol. Rev.*, 20, 1 (1968). For related compounds see Pace-Asciak et al., *Biochem.*, 10, 3657 (1971). Related compounds are described in a publication on 6-keto-prostaglandin F$_{1\alpha}$ by Pace-Asciak, *J. Am. Chem. Soc.*, 98, 2348 (1976) and a publication on "PGX" (6,9$\alpha$-oxido-9$\alpha$,15$\alpha$-dihydroxypros-ta(Z)5,(E)13-dienoic acid) by E. J. Corey et al., *J. Am. Chem. Soc.*, 99, 20016 (1977).

The potential pharmaceutical value of prostacyclins and prostacyclin analogs is described by S. Moncada, *Br. J. Pharmac.*, 76, 003–031 (1982) and by Honn et al. *Biochemical Pharmacology*, 32, 1–11 (1983).

The compounds of this invention may be regarded as analogs of prostacyclin and prostacyclin type compounds.

Prostacyclin, an organic compound related to prostaglandins, is (5Z)-9-deoxy-6,9$\alpha$-epoxy-$\Delta^5$-PGF$_1$. For its synthesis and structure see for example R. A. Johnson et al., *J. Am. Chem. Soc.*, 99, 4182 (1977) and *Prostaglandins*, 12, 915 (1976), and E. J. Corey et al., cited above. For some of its biological properties and uses see the references cited in the Johnson references.

Prostaglandins and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion, inhibition of tumor cell metastasis, and reduction of undesirable gastrointestinal effects from systemic administration of prostaglandin synthetase inhibitors.

Because of these biological responses, prostaglandins and prostacyclin-type compounds are useful to study, prevent, control, or alleviate a wide variety of diseases and undersirable physiological conditions in mammals. In accordance with the present invention, such mammals include humans, useful domestic animals, pets, and zoological specimens, and laboratory animals, such as mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi or tumor cell metastasis in mammals, including man, rabbits, and rats. For example, these compounds are useful in the treatment and prevention of myocardial infarcts, to treat and prevent postoperative surgery, and to treat conditions such as atherosclerosis, hypertension, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administraton is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart lung machines. Additionally, whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the perfused body portion, attached or detached, to the recipient, or to two or all of those at a whole blood. These compounds are also useful in preparing platelet-rich concentrates from blood for use in treating thrombocytopenia or in chemotherapy.

Prostaglandins E and F and related compounds are extremely potent in causing stimulation of smooth muscle, and are also highly active in potentiating other known smooth muscle stimulators, for example, oxytocic agents, such as oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the later purpose, the compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostaglandins and prostacyclin-type compounds are also useful in mammals, including man and certain useful animals, such as dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.01–20 μg. per kg. of body weight per minute, or in a total daily dose by injection of infusion in the range about 0.01 to about 10 mg. per kg. of body weight per day, the exact dose depending on the age, weight, and condition of the patient or animal, and on the frequency and route of administration.

Prostaglandins and prostacyclin-type compounds and their analogs are also useful in mammals, including man, to treat primary neoplasms and other cancers or tumors by inhibiting the production of metastasis away from the primary lesion. These compounds can be used singularly or in combination with other anti-metastatic treatment such as chemotherapy and radiation therapy. See Honn et al., *Biochemical Pharmacology*, 32, 1–11 (1983), for mechanisms by which prostacyclins (PGI$_2$) are thought to prevent the metastasis by inhibiting the association of the released tumor cells with platelets and/or the blood vessel wall thereby inhibiting the formation of new metastatic foci away from the primary lesion.

To treat with an anti-metastatic amount of the prostaglandin or prostatcyclin type compound, the compound is administered by infusion or injection, intravenously, subcutaneously or intramuscularly in an infusion dose range of about 0.001–5 mg/kg of body weight per minute, or in a total daily dose by injection in the range of about 0.01 to 10 mg/kg of body weight per day, the exact dose depending upon the age, weight and condition of the patient or animal, and on the frequency and route of administration.

Prostaglandins and prostacyclin-type compounds are also useful in reducing the undesirable gastrointestinal effects resulting from systemic administration of anti-inflammatory prostaglandin synthetase inhibitors, and are used for that purpose by concomitant administration of prostaglandins or prostacyclin-type compound and anti-inflammatory prostaglandin synthetase inhibitor. See Partridge et al., U.S. Pat. No. 3,781,429, for a disclosure that the ulcerogenic effect induced by certain non-steroidal and steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. Prostaglandins and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory cyclooxygenase inhibitor, for example indomethacin, aspirin, or phenylbutazone, is administered in any of the ways known in the art to alleviate an inflammatory condition, for example, in any dosage regimen and by any of the known routes of systemic administration.

The prostaglandins or prostacyclin-type compound is administered along with the anti-inflammatory prostaglandin synthetase inhibitor either by the same route of administration or by a different route. For example, if the anti-inflammatory substance is being administered orally, the prostaglandins or prostacyclin-type compound is also administered orally. Alternatively, it is administered rectally in the form of a suppository. In the case of women, the substance is administered vaginally in the form of a suppository or a vaginal device for slow release, such as described in U.S. Pat. No. 3,545,439. Alternatively, if the anti-inflammatory substance is being administered rectally, the prostaglandin or prostacyclin-type compound is also administered rectally. Further, the prostaglandin or prostacyclin derivative can be conveniently administered orally or, in the case of women, vaginally. It is especially convenient when the administration route is to be the same for both anti-inflammatory substance and prostaglandin or prostacyclin-type compound to combine both into a single dosage form.

The dosage regimen for the prostaglandin or prostacyclin-type compound in accord with this treatment will depend upon a variety of factors, including the type, age, weight, sex and medical condition of the mammal, the nature and dosage regimen of anti-inflammatory synthetase inhibitor being administered to the mammal, the sensitivity of the particular prostaglandin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of anti-inflammatory substance is causing undersirable gastrointestinal effects in the human or animal subject and to prescribe an effective amount of the prostaglandin or prostacyclin-type compound to reduce and then substantially to eliminate those undesirable effects.

Prostaglandin or prostacyclin-type compounds are also useful in the treatment of asthma. For example, these compounds are useful as bronchodilators or as inhibitors of mediators, such as SRS-A, and histamine which are released from cells activated by an antigen antibody complex. Thus, these compounds control spasm and facilitate breathing in conditions such as bronchial asthma, bronchitis, pneumonia and emphysema. For these purposes, these compounds are administered in a variety of dosage forms, such as orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 μg. per kg. of body weight are used 1 to 4 times a day, the exact dose depending on the age, weight, and condition of the patient and on the frequency and route of administration. For the above use the prostaglandin or prostacyclin-type compound can be combined advantageously with other asthmatic agents, such as sympathomimetics (isoproterenol, phenylephedrine, ephedrine, etc.); xanthine derivatives (theophylline and aminophylline); and corticosteroids (ACTH and prednisolone).

Prostaglandin or prostacyclin-type compounds are effectively administered to human asthma patients by oral inhalation or aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the above ingredient suspended in an inert propellant (such as a mixture of dichloro-difluoromethane and dichloro-tetrafluoroethane) together with a co-solvent, such as ethanol, flavoring materials and stabilizers. Instead of a co-solvent there can be used a dispensing agent such as oleyl alcohol. Suitable means to employ the aerosol inhalation therapy technique are described fully in U.S. Pat. No. 2,868,691 for example.

Prostaglandins or prostacyclin-type compounds are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart, the microvasculature serving the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, nonobstructive mesenteric ischemia, artritis lymphangitis and the like. These examples are included to be illustrative and should not be construed as limiting the term peripheral vascular disease. For these conditions the prostacyclin compounds are administered orally or parentally via injection or infusion directly into a vein or artery.

The dosages of such compounds are in the range of 0.01–10 $\mu$g. kg. administered by infusions at an hourly rate or by injection on a daily basis, such as one to four times a day. The exact dose depends on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No. 74/0149 referenced as Derwent Farmdoc No. 58,400V. See Elliott et al., *Lancet*, Jan. 18, 1975, pp. 140–142. Prostaglandins or prostacyclin-type compounds are useful in place of oxytocin to induce labor in pregnant female animals with intrauterine death of the fetus from about 20 weeks to term. For this purpose, the compound is infused intravenously at a dose of 0.01 to 50 $\mu$g. per kg. of body weight per minute until or near the termination of the second stage of labor i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostaglandins or prostacyclin type compounds are further useful for controlling the reproductive cycle in menstruating female mammals, including humans. By the term menstruating female mammals is meant animals which are mature enough to menstruate, but not so old that regular menstruation has ceased. For that purpose the prostaglandin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostaglandin or prostacyclin-type compounds are futher useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandin compounds is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, the prostacyclin compound is administered locally or systemically.

The prostaglandin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostaglandins and prostacyclin-type compounds are further useful in domestic animals as abortifacients (especially for feedlot heifer), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin or prostacyclin-type compound is injected or applied in a feed at doses of 0.1–100 mg. per animal and may be combined with other agents such as steroids. For example, mares are given the prostaglandin compound 5 to 8 days after ovulation and return to estrus. Cattle are treated at regular intervals over a 3 week period to advantageously bring all into estrus at the same time.

Prostaglandin or prostacyclin-type compounds increase the flow of blood in the mammalian kidney, thereby increasing volume and electrolyte content of the urine. For that reason, these compounds are useful in managing cases of renal dysfunction, especially those involving blockage of a renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or 0.001 to 10 μg. per kg. of body weight per minute until the desire effect is obtained. Subsequent doses are given by intravenous, intramuscular, or subcutaneous injection or infusion in the range 0.05 to 2 mg. per kg. of body weight per day.

Prostaglandin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosia, premalignant sun-induced keratosis, nonmalignant keratosis, acne, and seborrheic dermatitis in humans and atopic dermatitis and mange in domesticated animals. These compounds alleviate the symptoms of these proliferative skin disease. Psoriasis, for example, is alleviated when a scale-free psoriasis lesion is noticeably decreased in thickness or noticeably but incompletely cleared or completely cleared.

For those purposes, such compounds are applied topically as compositions including a suitable pharmaceutical carrier, for example as an ointment, lotion paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostaglandin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

Antiplatelet substances such as $PGI_2$ are known and have been used to afford relief from the aggregate condition.

$PGI_2$ is a notably unstable substance. Although effective, $PGI_2$ often affords unwanted hypotensive effects. However, there may be occasions when such a hypotensive effect is desirable, such as in the treatment of hypertension. Also the antiplatelet aggregation effect is short lived (and the hazardous condition associated with uncontrolled platelet aggregation returns quickly). The stability of $PGI_2$ as a medicine is not satisfactory because its half life at physiological pH is only about several minutes. The instability of $PGI_2$ is considered to be due to the fact that chemically the vinyl ether structure containing a double bond at $\Delta^5$ is readily hydrated to 6-oxoprostaglandin $F_{1\alpha}$ and in vivo, it is rapidly metabolized by a 15-position dehydrogenase. On the other hand, $PGI_2$ is considered to be not entirely satisfactory in its pharmacological actions because its doses required for platelet aggregation inhibiting action and antihypertensive action are almost equal to each other and its selectivity of action as a medicine is inferior. Accordingly, a considerable effort has been made in the art to synthesize many kinds of $PGI_2$ and remedy the aforesaid defects of $PGI_2$ (see, for example, S. M. Roberts, Chemistry, *Biochemistry & Pharmacological Activity of Prostanoids,* Pergamon Press, Oxford, 1979; New Synthetic Routes to *Prostaglandins and Thromboxanes,* Eds S. M. Roberts and F. Scheinmann, Academic Press, 1982). Additional examples of stabilized $PGI_2$ structures can be found in European patent application No. 0054795A2 and 195379A.

PGI derivatives and prostacyclin derivatives are well known in the art as described above. U.S. Pat. Nos. 4,123,444 and 4,124,599 described PG derivatives namely prostacyclins. These patents describe 5 and 6 keto substituents as well as 9-deoxy-9-deoxo-9-hydroxymethyl substituents. The patents are described as having general prostaglandin activity. U.S. Pat. No. 4,145,535 relates to certain trans-4,5-didehydro-PGI compounds which are also stated to exhibit general prostacyclin like properties. U.S. Pat. No. 4,233,121 describes certain 5-halo-6,9-oxido prostaglandin derivatives which have anticoagulant activity. European patent application No. 0054795A2/1982 discloses novel 5 or 7 monohalogenated or 5,7-dihalogenated prostacyclins useful for controlling vascular actions and inhibiting tumor metastasis.

FIG. 1—Discloses the numbering system of the allenic prostacyclin compounds of this invention.

SUMMARY OF THE INVENTION

The present invention particularly provides a compound of the formula:

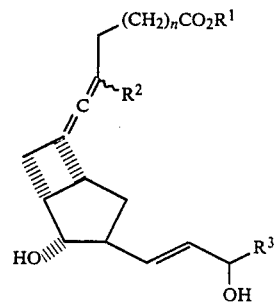

wherein:

n is 0, 1, 2

$R^1$ is hydrogen, lower alkyl, lower hydroxyalkyl, or a pharmaceutically acceptable cation;

$R^2$ is hydrogen, lower alkyl, cycloalkyl, heteroalkyl, halogen, aryl, alkylthio, phenylthio, alkylsulfinyl, phenylsulfonyl, or trifluoromethyl;

$R^3$ is a lower alkyl, a cycloalkyl, phenyl, benzyl, a cycloheteroalkyl, a lower alkyl having one to eight carbons substituted with one or more fluorines or containing 1 or 2 unsaturated bonds; and carbon 15 may be in the R or the S configuration, or a mixture of R and S with the proviso that when $R^1$ is a lower alkyl or lower hydroxyalkyl that carbon 15 is not in the R configuration.

The allenic prostacyclins of the present invention represent novel chemical structures that are chemically stable in the dry state or in solution as a sodium, potassium or calcium salt. The allenic compounds of the present invention unlike the prior art prostacyclin compounds unexpectedly were found to cause fewer undesirable effects.

Lower alkyl is a straight or a branched chain having one to eight carbons. Cycloalkyl is a cyclic compound containing three to seven carbons. Cycloheteroalkyl is a cyclic compound with two or six carbons and one oxygen or one sulfur. Lower hydroxyalkyl is a straight or a branched chain having from one to about eight carbon atoms. Heteroaryl is an aromatic ring system having 5 or 6 ring atoms wherein one such ring atom is nitrogen, oxygen, or sulfur, and the other such ring atoms are carbons. Alkylthio is a sulfur substituted with a lower alkyl. Alkylsulfonyl is a sulfonyl function substituted with a lower alkyl. A pharmaceutically acceptable cation is cation that, when combined to form a salt with an anion such as a carboxylate function, is generally considered suitable for human consumption.

$R^1$ may be a lower hydroxyalkyl or lower alkyl, such as methyl, ethyl, propyl, butyl and the like. $R^1$ may be hydrogen or any pharmaceutically acceptable cation, such as sodium, potassium, calcium, or a quaternary alkyl ammonium ion.

$R^2$ may be a lower alkyl, such as methyl, ethyl, propyl, butyl, pentyl, hexyl, heptyl, octyl and the like; a cycloalkyl such as cyclopropyl, cyclobutyl, cyclopentyl, cyclohexyl and the like; a heteroaryl, such as pyridyl, furyl, or thienyl phenyl; a halogen such as fluorine, chlorine or bromine; an alkylthio, such as methylthio; phenylthio; an alkyl sulfinyl, such as methylsulfinyl; phenylsulfinyl; or trifluoromethyl.

$R^3$ may be cycloalkyl containing four to seven carbon atoms, such as cyclobutyl, cyclopentyl, cyclohexyl, cycloheptyl and the like. $R^3$ may be a cycloheteroalkyl, such as tetrahydropyranyl, tetrahydrofuranyl, tetrahydrothiopyranyl and the like. $R^3$ may be lower alkyl containing 1 or 2 unsaturated bonds, that is, lower alkene or lower alkyne. $R^3$ may be lower alkene, such as ethylene, propylene, 1-butene, 2-butene, 1-pentene, 2-pentene, 3-pentene, 1-hexene, 2-hexene, 1-heptene, 2-heptene, 1-octene, 2-octene and the like. $R^3$ alkenes may be in either the cis or trans configuration. $R^3$ may be lower alkyne, such as acetylene, propyne, 1-butyne and the like, 1-pentyne and the like, 1-hexyne and the like, 1-heptyne and the like, and 1-octyne and the like, and may be optionally substituted by methyl, dimethyl or fluoro. $R^3$ may be a lower alkyl such as ethyl, propyl, butyl, pentyl, hexyl, heptyl or octyl and may be optionally substituted by fluoro. $R^3$ may also be phenyl or benzyl.

The term "carbon 15" refers to the side-chain carbon labeled as 3 in FIG. 1. To maintain consistency with usual prostanoid numbering schemes, the central allenic carbon is labeled "5" and the term "carbon 15" is applied to the same side-chain carbon, regardless of whether n is 0, 1, or 2. In accordance with the present invention, it is understood that the configuration of carbon 15 is the same whether the nomenclature S or R* is used. Accordingly, the terminology 15(S) is equivalent to 3R*. Both nomenclature conventiums are used interchangeably in this application. Likewise, the terminology 15(R) is equivalent to 3S*. In accordance with the present invention, carbon 15 may have the R or S configuration or be a mixture thereof with the proviso that when $R^1$ is a lower alkyl or hydroxy alkyl that carbon 15 is not in the R configuration.

FIG. I ALLENE PROSTACYCLIN

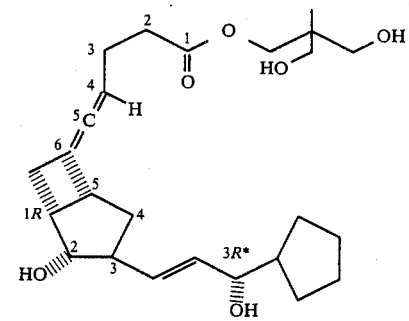

3R* = 15(S)

SCHEME I

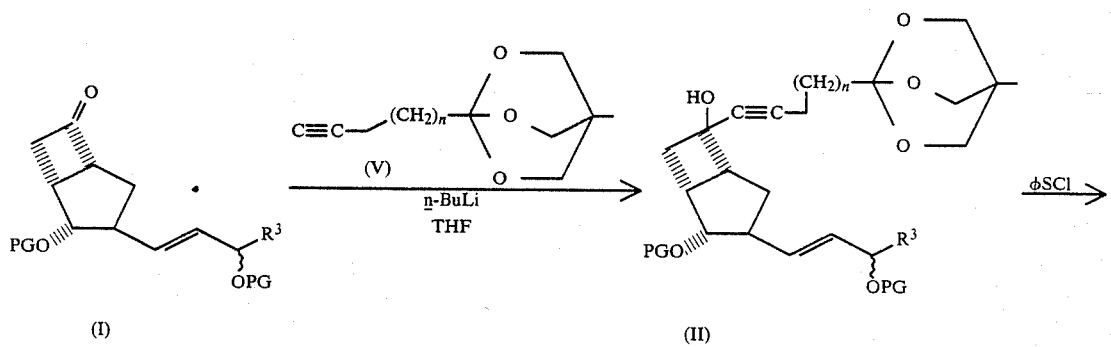

SCHEME I
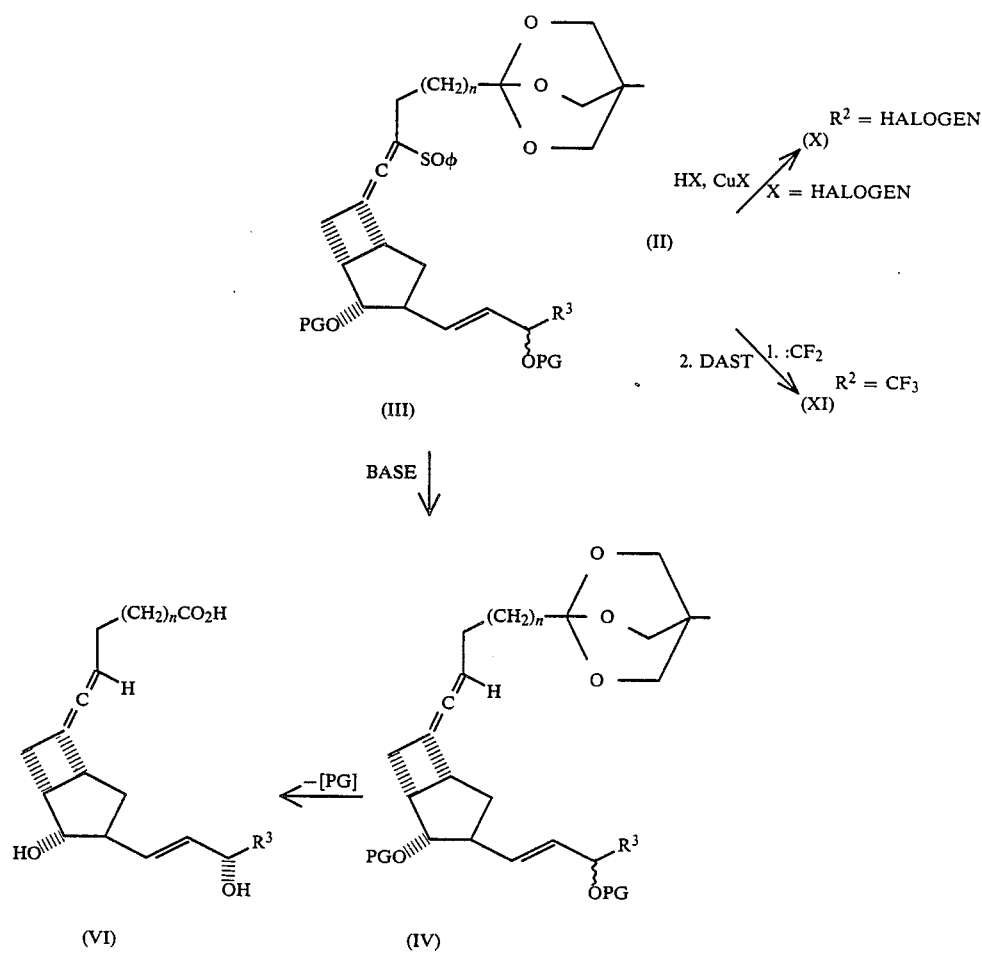
PG = PROTECTING GROUP
⋮⋮⋮ = BOND OF UNDEFINED STEREOCHEMISTRY
SCHEME II
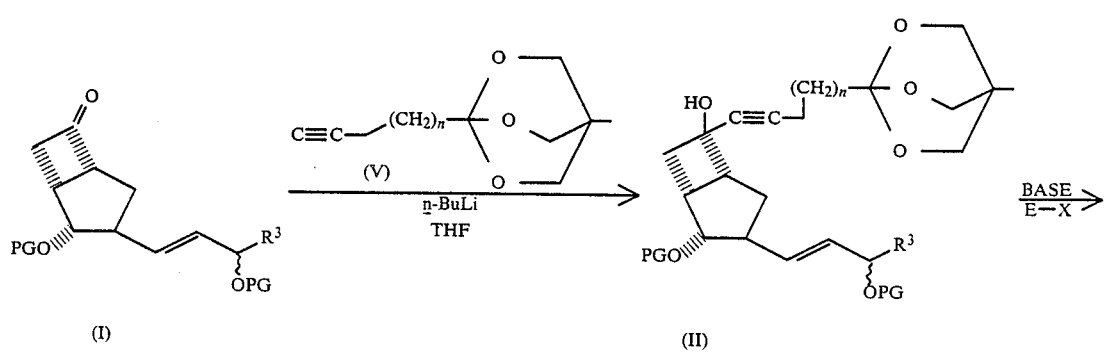

-continued
SCHEME II

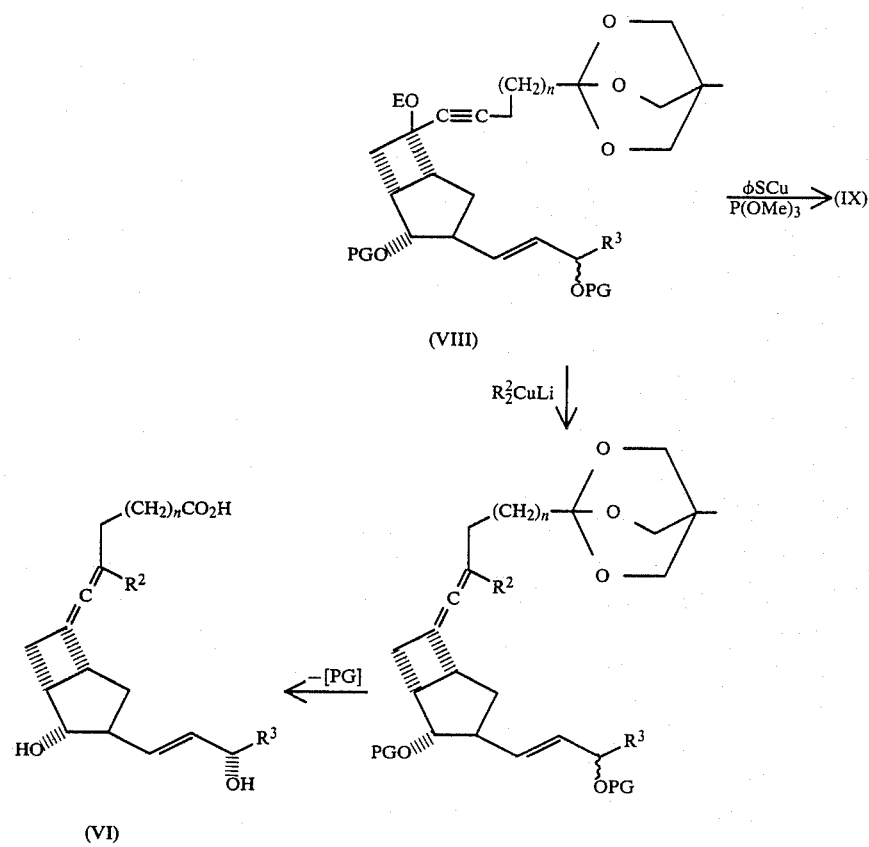

(VI)

PG = PROTECTING GROUP

⋍ = BOND OF UNDEFINED STEREOCHEMISTRY

E = ELECTROPHILE
X = LEAVING GROUP
$R^2$ = ALKYL, ARYL OR HETEROARYL

DESCRIPTION OF THE PREFERRED EMBODIMENTS

General Method

The allenic carbacyclins of this invention may be obtained as outlined in Scheme I or II or a modification thereof.

The starting material for Scheme I(I) are obtained as in E. J. Corey and N. Rajer, *Tetrahedron Letters,* 24, 5571 (1983); R. J. Cave, C. C. Howard, G. Koimkert, R. F. Newton, D. P. Reynolds, A. H. Wadsworth and S. M. Roberts, *J. Chem. Soc.,* 2984 (1979). $R^3$ can be adjusted as necessary. (For synthesis of different $R^3$s see *Prostaglandin Synthesis,* J. S. Bindra and R. Bindra, Academic Press 1977, p. 462.)

PG is a suitable protecting group, e.g. ethoxyethyl, tetrahydropyranyl or trialkylsilyl.

Treatment of this bicyclic ketone(I) with an acetylide anion of the type V (generated from the alkyne and an appropriate base such as n-butyl lithium; see, for example, E. P. Oliveto in J. Fried and J. A. Edwards, *Organic Reactions in Steroid Chemistry,* Vol. II, Van Nostrand Reinhold Comp., New York 1972, p. 139) provides an intermediate alkoxide which can be quenched with water to give the propargylic carbinol (II) or trapped with a suitable electrophile, such as acetic anhydride, to afford for example the propargylic acetate VIII [A propargylic sulfinate would be another possibility, see for example, H. Westmijze, I. Nap, J. Meijer, H. Kleijn and P. Vermeer, *Recl. Trav. Chim. Pays-Bas,* 102, 154 (1983) and references therein.] The carbinol (II) may be treated with an electrophile such as benzenesulfenyl chloride to afford the allenic sulfoxide (III) which can be converted to the allene using a base such as methyl lithium (see, V. Van Rheenen and K. P. Shephard, *J. Org. Chem.,* 44, 1583 (1979) and G. Neef, V. Eder and A. Seeger, *Tetrahedron Letters,* 21, 903 (1980)). The protecting groups, PG, can be removed upon exposure to acid or to a fluoride source such as tetrabutylammonium fluoride in tetrahydrofuran, or cesium fluoride in acetonitrile or diglyme. The ortho ester protecting group for the carboxyl can then be removed by sequential exposure to aqueous acid and base such as sodium, barium, lithium, potassium, and calcium hydroxide to give the salt where $R^1$=Na, Ba, Ca, Li, K and the like. This can be acidified to give the free acid where $R^1$=H. At this point, if an ester is required, the acid may be treated with an appropriate alkylating reagent/base combination e.g. ethyl iodide/DBU(R¹=Et). If a methyl ester is required, the acid may be reacted with diazomethane (R¹=CH₃). If an amide is required, the acid may be condensed with an appropriate amine, e.g. dimethylamine (Me₂NH), in the presence of a suitable dehydrating agent such as dicyclohexylcarbodiimide (R¹=NMe₂) or by other well known literature procedures.

The carbinol (II) can be utilized to access halogenated or trifluoromethylated allenes by procedures known in the literature (see, for example, *The Chemistry of the Allenes*, S. R. Landor Ed., Vol. I, Academic Press (1982)). For instance, a chloro-allene (X, R²=Cl) can be obtained by the reaction of (II) with a chlorinating agent such as thionyl chloride in an inert solvent such as ether in the presence of a base such as pyridine or triethylamine.

Alkylated allenes or sulfur containing allenes can be accessed as shown in Scheme II. The carbinol (II) can be converted to an acetate (VIII, R=Ac) or methanesulfinate (VIII, R=CH₃SO) as previously described.

Compounds of type VIII can be effectively converted into allenes by treatment with an appropriate organocopper reagent, e.g. dimethyl copper lithium (Me₂CuLi, 4 equivalents, 0° C., ether) which affords R²=CH₃. (For background on organocopper reagents, see G. Posner, *An Introduction to Synthesis using Organocopper Reagents*, Wiley-Interscience, 1980). Thioallenes (R²=S(Ph), SCH₃, and the like) can be accessed using VIII or another suitable intermediate using the procedure of A. J. Bridges and R. J. Ross, *Tetrahedron Letters*, 24, 4797 (1983). In which a propargylic, mesylate, triflate or methanesulfinate is reacted with a organo thiocopper complex in a solvent such as methylene chloride or benzene.

The compounds of the instant invention are novel in that, compared to natural occurring PGI₂, they are surprisingly more stable and are active against platelet aggregation over a longer period of time.

By virtue of this anti-platelet aggregation activity the compounds in accordance with the present invention are useful in treating platelet dysfunction in human and animals. A physician or veterinarian of ordinary skills could readily determine a subject who is exhibiting platelet dysfunction symptoms. Regardless of the route of administration selected, the compounds of the present invention are formulated into pharmaceutically acceptable dosage forms by conventional methods known to the pharmaceutical arts.

The compounds can be administered in such oral unit dosage forms such as tablets, capsules, pills, powders, or granules. They also may be administered rectally, vaginally in such forms as suppositories or creams; they may also be introduced in the form of eye drops, parenterally, subcutaneously, or intramuscularly, using forms known to the pharmaceutical art. In general, the preferred form of administration is orally.

An effective but non-toxic quantity of the compound is employed in treatment. The dosage regimen for preventing or treating platelet dysfunction by the compounds of this invention is selected in accordance with a variety of factors including the type, age, weight, sex, and medical condition of the mammal, the severity of the symptoms, the route of administration and the particular compound employed. An ordinarily skilled physician or veterinarian will readily determine and prescribe the effective amount of the agent to prevent or arrest the progress of the condition. In so proceeding, the physician or veterinarian could employ relatively low dosages at first, subsequently increasing the dose until a maximum response is obtained.

The acidic compounds of this invention can also be administered as pharmacologically acceptable basic salts such as sodium, potassium and calcium.

EXPERIMENTAL SECTION

¹H and ¹³C NMR spectra were recorded on a Varian FT80 or XL200 spectrometer at 80 or 200 MHz with chemical shifts reported in parts per million (δ) downfield from tetramethylsilane as an internal standard. Splitting patterns are designated as s, singlet; d, doublet; t, triplet; q, quartet; and m, multiplet.

Infrared spectra (IR) were obtained as solution in chloroform (CHCl₃) and are given in cm⁻¹. (Only major frequencies are recorded.) Mass Spectra were run on a Kratos MS30 or MS50 at 70 eV and an ionizing current of 300 mA.

EXAMPLE 1

(1R,1α,5α-[3R*-cyclopentyl-3-[[(1,1-dimethylethyl)di methylsilyl]oxy]-1E-propenyl]-2β-[[(1,1-dimethylethyl)dimethylsilyl]oxy]-6-[4-(4-methyl-2,6,7-trioxabicyclo[2.2.2]oct-1-yl)-1-butynyl]-6-bicyclo[3.2.0]heptan-6-ol (3)

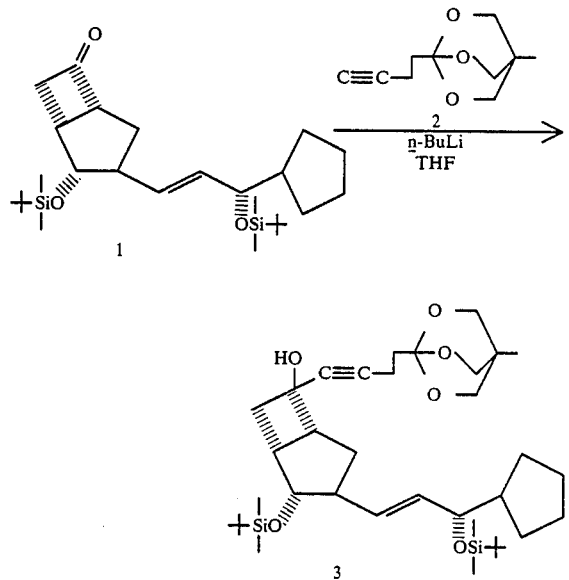

Compound (2) (74 mgs) was dissolved in dry THF (3 cm³) with stirring under argon at 0° C. A solution of n-butyl lithium (1.58N in hexane, 0.26 cm³) was added via syringe and the mixture stirred at 0° C. for 20 mins. At this point, a solution of (1) in dry THF (97 mgs in 1 cm³) was added to the reaction mixture (cooled to −20° C.) and the mixture allowed to warm back to 0° C. and stirred at that temperature for 30 mins. The reaction mixture was poured into water and thoroughly extracted with ether. The combined organic extracts were washed with brine and dried (Na₂SO₄). Evaporation of the solvent in vacuo afforded 150 mgs of crude product, which was purified by chromatography on silica gel using ethyl acetate/hexane/triethylamine (5:95:0.5) as eluent. 51 mgs of pure product were obtained.

NMR (1H, δ, CDCl₃, 80 MHz) 0.1 (12H, (CH₃)₂Si—), 0.8 (3H, s, orthoester CH₃), 0.85 (18H, (CH₃)₃C—Si), 1.0–2.25 (21H, m, cycloalkyl Hs and α-chain Hs), 3.8 (6H, s, ortho ester CH₂s), 3.6–4.0 (2H, m, CH—OSi), 5.25–5.75 (2H, m, olefinic Hs).

MS[m/e] 660, 603, 459, 235, 171, 144, 73. ac. mass. calculated for C₃₇H₆₄O₆Si 660.4222; found 660.4219.

EXAMPLE 2

1-[4-[(1R,1α,5α)-3α-[3R*-cyclopentyl-3-[[(1,1-dimethylethyl)dimethylsilyl]oxy]-1E-propenyl]-2β-[[(1,1-dimethylethyl)dimethylsilyl]oxy]bicyclo[3.2.0]hept-6-ylidene]-3-(phenylsulfinyl)-3-butenyl]-4-methyl-2,6,7-trioxabicyclo[2.2.2]octane

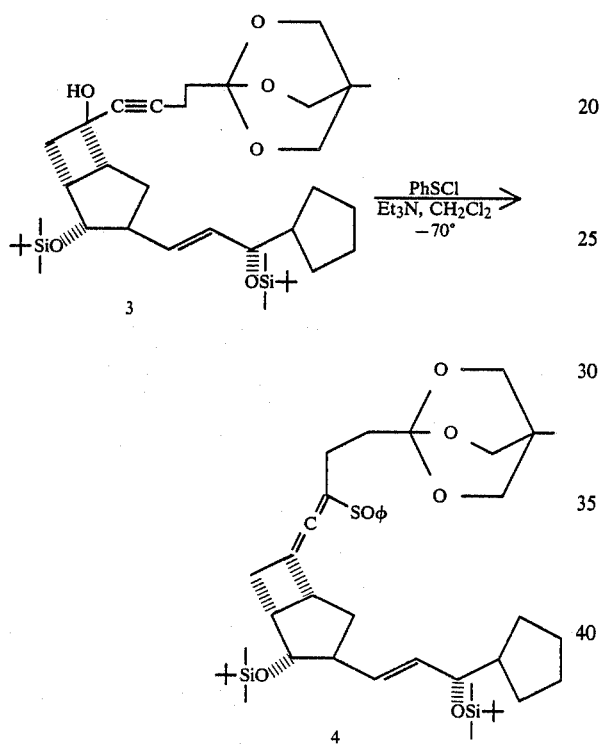

Compound (3) (0.15 g, 0.23 mMol) was dissolved in distilled dichloromethane (5 cm³) and distilled triethylamine (36 mgs) added via syringe. The mixture was cooled to −70° C. under argon and then benzenesulfenyl chloride (38 mgs, 1.2 equivalents) was added dropwise as a solution in dichloromethane. The mixture was stirred at −70° C. for 1 hour and then at −20° C. for 35 minutes. At the end of this time, the mixture was partitioned between dichloromethane and dilute potassium bicarbonate. The organic layer was separated and washed with brine and dried (Na₂SO₄). Evaporation of the volatiles in vacuo afforded 160 mgs of material which was purified by chromatography on silica gel to afford 57 mgs of allene sulfoxide (4) and 80 mgs of recovered starting material (3).

NMR (1H, δ, CDCl₃, 80 MHz), 0.1 (12H, (CH₃)₂Si—), 0.8 (3H, s, orthoester CH₃), 1.0–2.25 (21H, m, cycloalkyl Hs and α-chain Hs), 3.8 (6H, s, orthoester CH₂'s), 3.6–4.0 (2H, m, CHOSi), 5.35–5.65 (2H, m, olefinic Hs), 7.4–7.6 (5H, m, aromatic Hs).

MS(m/e) 768, 711, 368, 185, 73. C₄₃H₆₈O₆Si₂S requires 768.4301; found 768.4305.

EXAMPLE 3

1-[4-[(1R,1α,5α)-3α[3R*-cyclopentyl-3-[[(1,1-dimethylethyl)dimethylsilyl]oxy]-1E-propenyl]-2β-[[(1-dimethylethyl)dimethylsilyl]oxy]bicyclo[3.2.0]hept-6-ylidene]-3-butenyl]-4-methyl-2,6,7-trioxabicyclo[2.2.2]octane

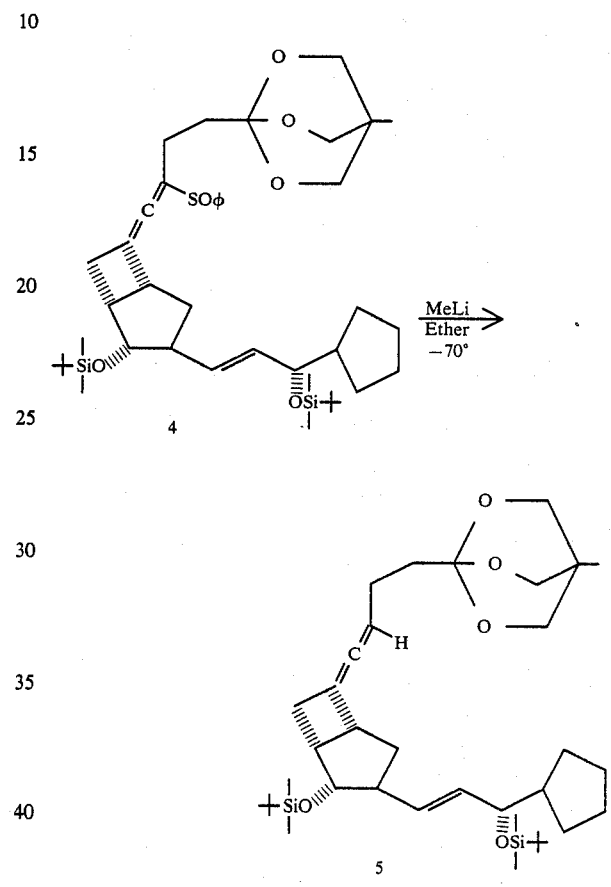

Compound (4) (72 mgs, 0.1 mol) was dissolved in dry ether (5 cm³) and the solution cooled to −70° C. A solution of methyl lithium in ether (1.7M, 1.75 cm³, 4 equivalents) was added via a syringe and the mixture stirred magnetically under argon for 15 minutes. The reaction mixture was poured into saturated ammonium chloride and extracted thoroughly with ether. The combined organic extracts were washed with brine and then dried (Na₂SO₄). Evaporation of the volatiles in vacuo afforded, after chromatography of the residue on silica gel, (eluting with ethylacetate/hexane/Et₃N 5:94.8:0.2), 42 mgs of (5).

NMR (1H, δ, CDCl₃, 80 MHz) 0.1 (12H, (CH₃)₂Si—) 0.8 (3H, s, orthoester CH₃), 0.85 (18H, (CH₃)₃C—Si), 1.0–2.25 (21H, m, cycloalkyl Hs and α-chain Hs), 3.8 (6H, s, orthoester CH₂'s), 3.6–4.0 (2H, m, CH—OSi), 5.1 (1H, m, allene H), 5.35–5.65 (2H, m, olefinic Hs).

MS(M/e) 644, 575, 529, 513, 485, 443, 413, 275, 213, 197, 171, 73. C₃₇H₆₄O₅Si₂ required 644.4292; found 644.4292.

EXAMPLE 4

(1R,1α,5α)-3α-(3R*-cyclopentyl-3-hydroxy-1E-propenyl)-6-[4-(4-methyl-2,6,7-trioxabicyclo[2.2.2]oct-1-yl)-1-butenylidene]bicyclo[3.2.0]heptan-2β-ol

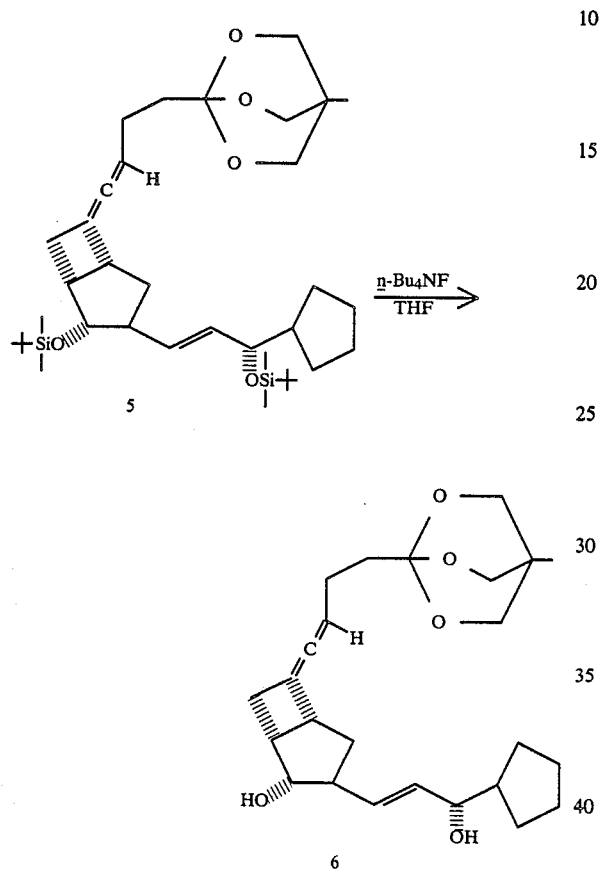

Compound (5) (40 mgs, 0.06 mmol) was dissolved in dry THF containing n-Bu₄NF (1 Molar in THF, 0.8 cm³) and the mixture stirred at 25° C. under argon for 2 days. The solvent was evaporated in vacuo and the residue partitioned between ethyl acetate and 2N sodium bicarbonate. The organic layer was separated, dried (Na₂SO₄) and evaporated in vacuo. Chromatography of the residue on silica gel, (EA/hexane/triethylamine, 8:2:0.2) afforded 25 mgs of product.

NMR (1H, δ, CDCl₃, 80 MHz) 0.8 (3H, s, orthoester CH₃), 1.0–2.25 (21H, m, cycloalkyl Hs and α-chain Hs) 3.8 (6H, s, orthoester CH₂'s), 3.75–4.0 (2H, m, CH—OH), 5.1 (1H, m, allene H), 5.55–5.75 (2H, m, olefinic Hs).

MS (M/e) 416, 398, 347, 329, 267, 263, 253, 248, 144, 123, 69 (C₂₅H₃₆OS required 416.2568; found 416.2562.

EXAMPLE 5

5-[(1R,1α,5α)-3α-(3R*-cyclopentyl-3-hydroxy-1E-propenyl)-2β-hydroxybicyclo[3.2.0]hept-6-ylidene]-4-pentenoic acid, sodium salt

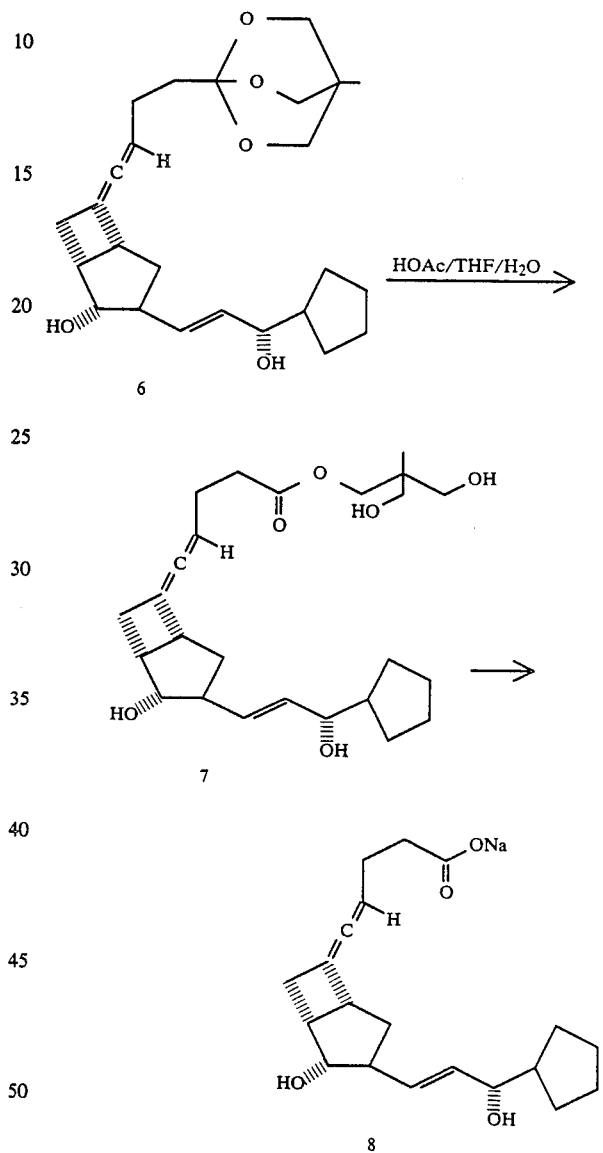

Compound (6) (25 mgs) was dissolved in a mixture of acetic acid, THF and water (3:1:1, 1 cm³) and the mixture stirred at 0° C. for 1 hour. A small aliquot was removed from the reaction mixture at this time and evaporated in vacuo to afford compound (7) 5 mgs. The rest of the material was warmed to 25° C. and evaporated in vacuo. The residue was dissolved in methanol containing one equivalent of sodium hydroxide (1M in water) and stirred until no more (7) was present. The solvent was removed under high vacuum and the residue triturated with ethyl acetate and redried under high vacuum. Thus obtained were 8 mgs. of (8).

EXAMPLE 6

(1R,1α,5α)-3α-[3R*-cyclopentyl-3-[[(1,1-dimethylethyl)dimethylsilyl]oxy]-1E-propenyl]-2β-[[(1,1-dimethylethyl)dimethylsilyl]oxy]-6-[4-(4-methyl-2,6,7-trioxabicyclo[2.2.2]oct-1-yl)-1-butynyl[bicyclo[3.2.0]-]heptan-6-ol, acetate

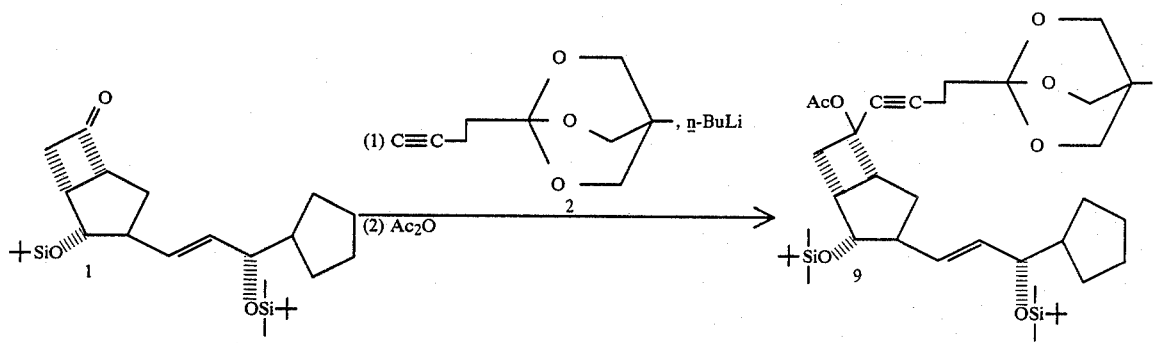

Compound (2) (1 mMol) was dissolved in dry THF with stirring under argon at 0° C. A solution of n butyl lithium (1 equivalent) in hexane was added via syringe and the mixture stirred at 0° C. for 20 minutes. At this point, a solution of (1) (1 mmol) in THF was added to the reaction mixture (cooled to −20° C.) and the mixture allowed to warm back to 0° C. and stirred at that temperature for 30 mins. The mixture was recooled to −20° C. and quenched with neat acetic anhydride (1.2 equivs.) The mixture was warmed to 20° C., poured into 2N sodium bicarbonate solution, and thoroughly extracted with ether. The combined organic extractions were washed with brine and dried ($Na_2SO_4$). Evaporation of the solvent in vacuo afforded crude (9) which was purified by chromatography on silica gel.

EXAMPLE 7

1-[4-[(1R,1α,5α)-3α-[3R*-cyclopentyl-3-[[(1,1dimethylethyl)dimethylsilyl]oxy]-1E-propenyl]-2β-[[(1,1-dimethylethyl)dimethylsilyl]oxy]bicyclo]3.2.0]hept-6-ylidene]-3-methyl-3-butenyl]-4-methyl-2,6,7-trioxabicyclo[2.2.2]octane

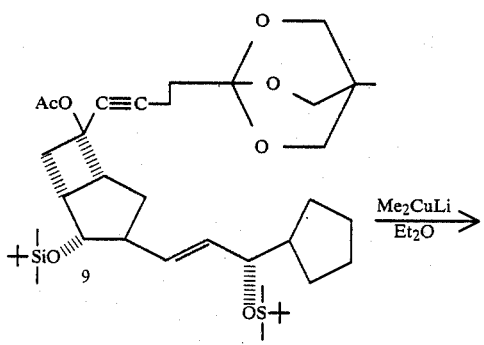

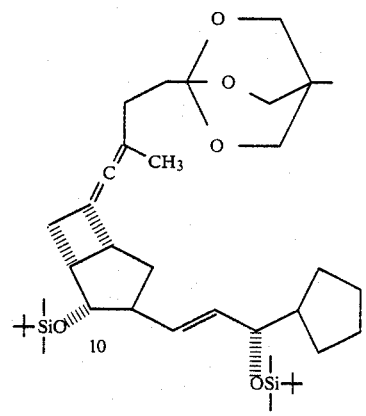

Compound (9) 1 mmol in dry $Et_2O$ (2 cm³ was added via syringe to a solution of lithium dimethylcuprate (4 equivalents) in ether at −20° C. (magnetic stirring, argon). The reaction mixture was stirred at 5° C. for 2 hours and then quenched with $NH_4Cl$ solution. The mixture was thoroughly extracted with ether and the combined extracts were washed with water, brine and then dried ($Na_2SO_4$). Evaporation of the volatiles in vacuo afforded crude (10) which was purified by chromatography on silica gel.

EXAMPLE 8

(1R,1α,5α)-3α-(3R*-cyclopentyl-3-hydroxy-1E-propenyl)-2-methyl-6-[4-(4-methyl-2,6,7-trioxabicyclo[2.2.2]oct-1-yl)-1-butenylidene]bicyclo[3.2.0]heptan-2β-ol

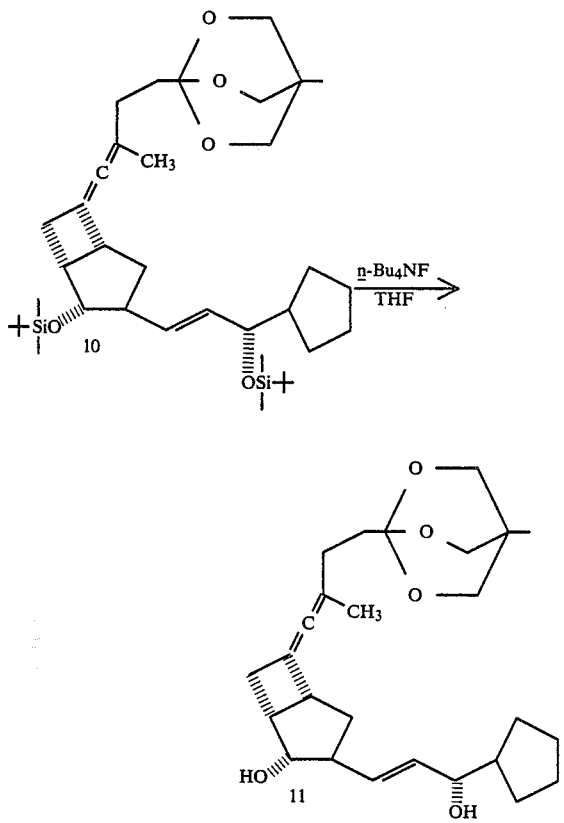

Compound (5) was dissolved in dry THF containing n-Bu₄NF (1 Molar in THF) and the mixture stirred at 25° C. under argon for 2 days. The solvent was evaporated in vacuo and the residue partitioned between ethyl acetate and 2N sodium bicarbonate. The organic layer was separated, dried (Na₂SO₄) and evaporated in vacuo. Chromatography of the residue on silica gel afforded pure product (11).

EXAMPLE 9

5-[(1R,1α,5α)-3α-(3R*-cyclopentyl-3-hydroxy-1E-propenyl)-2β-hydroxybicyclo[3.2.0]hept-6-ylidene]-4-methyl-4-pentenoic acid

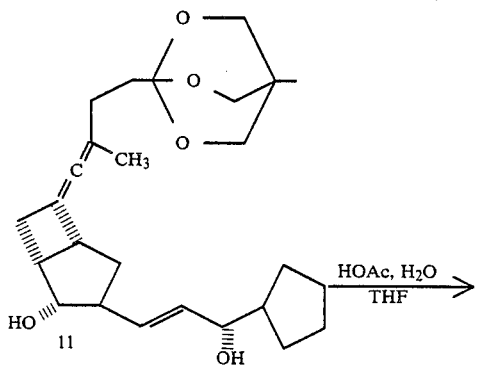

Compound (11) was dissolved in a mixture of acetic acid, THF and water (3:1:1) and the mixture stirred at 0° C. for 1 hour. A small aliquot was removed from the reaction mixture at this time and evaporated in vacuo to afford compound (12). The rest of the material was warmed to 25° C. and evaporated in vacuo. The residue was dissolved in methanol containing one equivalent of sodium hydroxide (1M in water) until no more (12) was present. The solvent was removed under high vacuum and the residue triturated with ethyl acetate and redried under high vacuum to afford compound (13).

BIOLOGICAL TESTING

The Inhibition of ADP-Induced Platelet Aggregation

The procedure for testing platelet anti-aggregatory activity in vitro is the following one described by E. R. Waskawic. Aggregation was determined with a Payton Dual Channel Aggregation module. A Riken-Denshi recorder was used for recording the aggregation curves.

Citrated whole blood (1 part 3.8% sodium citrate and 9 parts blood) was centrifuged to obtain platelet rich plasma (PRP) (700 RPM for 11 mins.) in an IE centrifuge (Model PR 6000). After the PRP fraction was removed, the remainder was spun at 900 xg for 15 mins. to obtain platelet poor plasma (PPP) (1800 RPM in IEC PR 6000). The number of platelets per ml PRP is determined by counting a 5 μl aliquot of PRP in a Coutter ZBI counter and channelyzer Model C-1000.

PRP is diluted with PPP 1:2 to obtain a count of approx. 25000 on the screen or $10^9$ platelets/ml PRP to evaluate the anti-aggregating agent. The module was standardized with an aliquot of PPP and that of diluted PRP.

The aggregating agent used is ADP prepared as follows: 4.7 mgs ADP (MW 427) in 10 ml saline yields a 10 μL PRP, of ADP disodium (MW=473).

| Vol. of stock (ml) | Volume of saline (ml) | [f] cuvette (mM) |
|---|---|---|
| 1.6 | 0.4 | 8 |
| 1.2 | 0.8 | 6 |
| 0.8 | 1.2 | 4 |
| 0.4 | 1.6 | 2 |
| 0.2 | 1.8 | 1 |

[f] = final concentration

Prostacyclin is used as the standard of antiaggregatory activity for determining the potency of compounds tested. A $10^{-2}$M solution (to give a starting concentration of $10^{-4}$M when 4 μL is added to 400 μL PRP) is diluted serially to obtain solutions with final concentrations of $10^{-6}$, $10^{-7}$, $10^{-8}$, $10^{-9}$M.

Compounds to be screened are dissolved in absolute ethanol, saline or water to achieve a $10^{-2}$M solution if 4 μL added to PRP giving a [f] in the cuvette equal to $10^{-4}$M. Serial dilutions in saline give $10^{-5}$, $10^{-6}$ and $10^{-7}$M.

1. Determine the dose of ADP which on a standard curve would be on the linear portion and allow reversal of the aggregation curve.

2. Determine the PGI$_2$ standard curve of percentage inhibition of aggregation. Use saline in control cuvette to compare the extent of inhibition by PGI$_2$ as represented by the depth of the aggregation curve. Allow the PRP to preincubate for approximately one minute prior to the addition of prostacyclin and another minute with PGI$_2$ prior to the addition of ADP.

% Inhibition of control =

$$100.00 - \left(\frac{\text{experimental parameter}}{\text{control parameter}} \times 100\right)$$

The % inhibition is plotted against prostacyclin dose on semilog paper. The IC$_{50}$ value is equal to the PGI$_2$ dose effecting 50% inhibition of the control response.

3. The test compound is added to PRP and preincubated for 1 minute prior to ADP administration. If the compound has an IC$_{50}$ lesser than $10^{-4}$M, it is considered to be active.

| BIOLOGICAL TESTING | |
|---|---|
| Compound | In Vitro Inhibition of ADP Induced Platelet Aggregation |
| 7 | $3 \times 10^{-6}$ M |

What we claim is:
1. A compound having the formula:

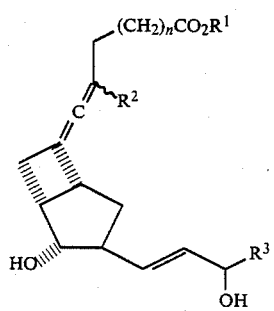

wherein:
n is 0, 1, 2
R$^1$ is hydrogen, lower alkyl, lower hydroxyalkyl, or a pharmaceutically acceptable cation;
R$^2$ is hydrogen, lower alkyl, cycloalkyl, heteroalkyl, halogen, aryl, alkylthio, phenylthio, alkylsulfinyl, phenylsulfonyl, or trifluoromethyl;
R$^3$ is a lower alkyl, a cycloalkyl, phenyl, benzyl, a cycloheteroalkyl, a lower alkyl having one or more fluorines or containing 1 or 2 unsaturated bonds; and carbon 15 may be in the R or the S configuration, or a mixture of R and S with the proviso that when R$^1$ is a lower alkyl or lower hydroxyalkyl that carbon 15 is not in the R configuration.

2. A compound according to claim 1 with the formula:

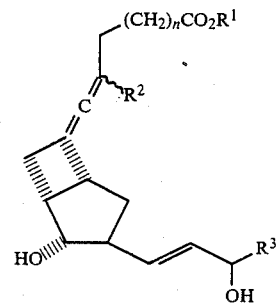

wherein: R$^2$ is hydrogen, lower alkyl having one to six carbons, cycloalkyl having three to seven carbons, heteroalkyl, halogen, aryl, alkylthio, alkylsulfinyl or trifluoromethyl.

3. A compound according to claim 1 with the formula:

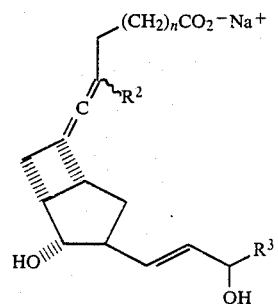

wherein: R$^2$ is hydrogen, lower alkyl having one to six carbons, cycloalkyl having three to seven carbons, heteroalkyl, halogen, aryl, alkylthio, alkylsulfinyl or trifluoromethyl.

4. A compound according to claim 3 which is 5-[(1R,1α,5α)-3α-(3R*-cyclopentyl-3-hydroxy-1E-propenyl)-2β-hydroxybicyclo[3.2.0]hept-6-ylidene]-4-pentenoic acid, sodium salt.

5. A compound according to claim 2 which is 5-[(1R,1α,5α)-3α-(3R*-cyclopentyl-3-hydroxy-1E-propenyl)-2β-hydroxybicyclo[3.2.0]hept-6-ylidene]-4-pentenoic acid.

6. A compound according to claim 1 wherein R$^1$ is hydrogen or a pharmaceutically acceptable cation and carbon 15 is in the R or S configuration or a mixture of R and S.

* * * * *